United States Patent [19]
Synodis et al.

[11] Patent Number: 5,571,519
[45] Date of Patent: Nov. 5, 1996

[54] ORGANOLEPTICALLY STABLE DENTURE CLEANSER TABLETS

[75] Inventors: Joseph Synodis, Summit; Robert C. Gasman, Milford; Frank Mazzella, Jersey City, all of N.J.

[73] Assignee: Block Drug Company, Inc., Jersey City, N.J.

[21] Appl. No.: 356,793

[22] Filed: Dec. 13, 1994

Related U.S. Application Data

[63] Continuation of Ser. No. 152,977, Nov. 15, 1993, abandoned.

[51] Int. Cl.⁶ .................................................. A01N 25/00
[52] U.S. Cl. ........................ 424/405; 424/401; 424/466; 424/49
[58] Field of Search .................................. 424/405, 401, 424/466, 49

[56] References Cited

U.S. PATENT DOCUMENTS

| | | | |
|---|---|---|---|
| 3,962,107 | 6/1976 | Levin et al. | 252/100 |
| 4,256,599 | 3/1981 | Krisp et al. | 252/99 |
| 4,267,164 | 5/1981 | Yeh et al. | 424/44 |
| 4,417,993 | 11/1983 | Gergely . | |
| 5,055,305 | 10/1991 | Young | 424/466 |
| 5,098,715 | 3/1992 | McCabe et al. | 424/479 |
| 5,240,415 | 8/1993 | Haynie | 433/216 |
| 5,270,031 | 12/1993 | Lim et al. | 424/49 |

FOREIGN PATENT DOCUMENTS

| | | |
|---|---|---|
| 0151203 | 2/1984 | European Pat. Off. . |
| 0248936 | 6/1986 | European Pat. Off. . |

*Primary Examiner*—Thurman K. Page
*Assistant Examiner*—William E. Benston, Jr.
*Attorney, Agent, or Firm*—Ostrolenk, Faber, Gerb & Soffen, LLP

[57] ABSTRACT

Denture cleanser tablet compositions are disclosed which include a flavoring agent in one layer and a bleaching agent in a second layer. This arrangement avoids deterioration of the tablet flavor and taste during storage.

19 Claims, No Drawings

ORGANOLEPTICALLY STABLE DENTURE CLEANSER TABLETS

This is a continuation of application Ser. No. 08/152,977 filed on Nov. 15, 1993 now abandoned.

BACKGROUND OF THE INVENTION

1. Field of the Invention

The present invention relates to denture cleanser compositions and, more particularly, denture cleanser tablet compositions which have long lasting flavor and taste.

2. Description of the Art

Conventional denture cleanser tablets are typically formulated with effervescent systems, bleaching agents, surfactants, builders, chelating agents and/or enzymes to remove unsightly stains and debris from dentures. The addition of flavor oils to denture cleanser tablet formulations has greatly increased the appeal of these products to consumers because they impart a fresh, for example minty, odor and taste to the dentures. However, it is known that tablet aroma changes during storage and studies have shown that denture cleanser tablet users are very sensitive to and are able to detect even slight changes in tablet aroma. Hence denture cleanser tablet aroma is a very important commercial attribute of these products. The known denture cleanser tablets, however, tend to have their aroma change during storage.

Layered denture cleansing tablets are known. U.S. Pat. No. 3,962,107 to Levin et al., for example, discloses a two layer denture cleanser tablet including an enzyme layer and an active oxygen layer. This formulation is designed to overcome the problem of the inactivating effect of the active oxygen compounds on the enzyme during the shelf life period as well as in the water solution when the tablet is placed in water with the dentures to be cleaned. In Levin's preferred composition, the enzyme layer contains sodium bicarbonate, polyvinyl pyrrolidone, magnesium lauryl sulfate, citric acid, polyethylene glycol 6000 and the enzyme. The active oxygen layer contains potassium monopersulfate, sodium perborate, citric acid, sodium bicarbonate, sodium lauryl sulfoacetate, polyvinyl pyrrolidone, magnesium lauryl sulfate and polyethylene glycol 6000. In one example, the flavorant in Levin's composition was incorporated in the enzyme layer. U.S. Pat. Nos. 4,256,599 to Krisp et al. and 4,417,993 to Gergely, and European Pat. Appl. Nos. 0151203 and 0248936 also disclose denture cleanser tablets having two layers.

The prior art, however, has not attempted to preserve the flavor and aroma of denture cleanser tablets using a layered arrangement. Indeed, the prior art has apparently not recognized the problem of flavor and/or aroma degradation, let alone the cause or solution of it.

It is an object of the present invention to provide layered denture cleanser tablet compositions having a fresh aroma and fresh taste even after prolonged storage. This and other objects will become apparent from the following description.

SUMMARY OF THE INVENTION

The foregoing objective is achieved by a denture cleanser tablet composition in accordance with the invention wherein a flavoring component of the tablet is isolated in a layer separate from the oxidant chemicals responsible for its deterioration. In particular, a multilayer denture cleanser tablet composition is provided which includes a flavoring agent located in a first layer and the oxidizing or bleaching agent or agents which deteriorate the flavoring agent located in a layer separate from the flavoring agents.

Multilayer enzymatic and non-enzymatic denture cleanser tablet compositions are also provided by the invention. The enzymatic composition includes a first layer containing the flavoring agent and a second layer containing the deterioration causing or producing agent and enzyme. The enzyme may be in a layer separate from the flavor and deterioration causing or producing agent. The product may also contain standard denture tablet ingredients. The non-enzymatic composition is substantially the same but does not include the enzyme.

Other features and advantages of the present invention will become apparent from the following description of the invention.

DETAILED DESCRIPTION OF THE INVENTION

Denture cleanser tablets in accordance with the invention may include any suitable flavorant or flavor oil. Preferred flavorants are the natural mint oils peppermint and spearmint, but other flavorants such as menthol, oil of wintergreen, and citrus flavors, such as lemon, lime and orange, may also be used. Other suitable flavorants and flavor oils will be apparent to one skilled in the art. The flavoring component is preferably present in the tablet in an amount within the range of about 0.05% to about 4.0% based upon the total tablet weight, and most preferably in an amount within the range of about 0.1% to about 2%.

Denture cleanser compositions in accordance with the invention contain one or more bleaching agents and may contain one or more of any of the known components of such compositions, such as surfactants, builders and chelating agents, excipients, effervescent systems, foam stabilizers and buffering systems. Appropriate levels of the components not discussed below and other suitable components in addition to those discussed, are conventional and will be apparent to one skilled in the art.

It has been found for example that the bleaching agents can be responsible for the deterioration of flavoring agent(s). Suitable bleaching agents include: activated or non-activated peroxygen bleaches, such as alkali metal perborate salts, for example, sodium perborate monohydrate, alkali metal peroxycarbonates, for example, sodium percarbonate, alkali metal persulfates, for example potassium monopersulfate, and organic acid peroxides for example, succinic acid peroxide, chlorine or hypochlorite generating materials, such as heteroxcyclic n-chloroimides, for example, sodium chloroisocyanurate chlorinated hydantoins, such as 1,3-dichloro-5,5-dimethylhydantoin, and, for example, Dactin™, and dry inorganic compounds such as calcium and sodium hypochlorite. The bleaching agent component is preferably present in the tablet in an amount within the range of about 1% to about 80%, based upon total tablet weight, and most preferably in an amount within the range of about 5% to about 55%.

Suitable surfactants include: anionics such as carboxylic acid salts, for example, sodium salts of straight chain fatty acids; sulfonic acid salts, such as linear alkylbenzene sulfonates ($C_{13}$–$C_{15}$), petroleum sulfonates, secondary n-alkanesulfonates, sulfosuccinate esters, sulfated linear primary alcohols ($C_{12}$–$C_{20}$), sulfated polyoxyethylenated straight chain alcohols, sulfated triglycerides; nonionics, such as polyoxyethylenated alkyl phenols, polyoxyethylenated mercaptans, long chain carboxylic acid esters, polyoxyethylenated straight-chain alcohols, alkanolamine condensates, N-alkylbetaines, N-alkyl-β-iminodipropionic acids, imidazoline carboxylates and sulfo-betaines; cationics, such as long chain amine hydrochlorides and polyoxyethylenated long chain amine hydrochlorides, for example, salts of primary amines derived from vegetable and animal fatty acids, tall oil or synthetic $C_{12}$–$C_{18}$ primary, secondary and tertiary amines, diamines and polyamines.

Suitable builders and chelating agents include: complex phosphates, such as sodium tripolyphosphate, sodium hexametaphosphate; alkali metal carbonates; alkali metal silicates; zeolites; and salts of carboxylic acids, such as sodium citrate; alkali metal salts of ethylenediamine tetraacetic acid; polymeric salts; and acrylic and maleic acids and their copolymers.

Suitable excipients include: binding compounds, such as polyvinyl-pyrrolidone and polyethylene glycols; lubricants, such as fumed silicas and alkali metal salts of saturated fatty acids; fillers, such as sodium sulfate, alkali metal acid carbonates and carbonates. Suitable effervescent systems, based on aqueous reactions, include: alkali metal carbonates or alkali metal persulfates with carboxylic acids; and alkali metal hydrogen carbonates in combination with carboxylic acids, such as citric acid or acid anhydrides; reactions of organic chlorine materials, such as heterocyclic N-chloroimides with peroxygen agents, such as alkali metal salts of perborate or peroxycarbonate; and other known carbon dioxide and/or oxygen liberating reactions common to compositions in this art.

Suitable buffering systems include: combinations of neutralized and free alkali metal carbonates, silicates, phosphates, carboxylic acids, and other ionizable species that influence the concentration of $(H^+)$, $(OH^-)$.

The compositions of the invention may be formulated as a multilayer (i.e., more than two layers) denture cleansing tablet, and may be enzymatic, if desired. If an enzyme is included in the tablet, all the enzyme is located in a layer of the tablet which does not contain the flavoring agent so as to avoid deterioration of the flavoring agent by the enzyme. The enzyme can also be in a layer which contains neither the flavoring agent or the bleaching agent. For instance, the tablet may have three layers, etc.

Any suitable enzyme material, such as those derived from various strains of *Bacillus subtilis* (also known as subtilisins) and *Bacillus licheniformis*, such as those sold under the trademarks Durazym, Esperase, Savinase, Maxatase, Alcalase and Endodextranase may be utilized in the tablets.

The tablets may be manufactured using conventional equipment and methods. See, for example, the U.S. patents and foreign patent applications and patents discussed above, the disclosures of which are all herein incorporated by reference.

The following examples illustrate the invention:

EXAMPLE 1

One and two layer tablets were prepared for sensory evaluations. First a granulated mixture containing 82.7% sodium bicarbonate, 14.6% sodium hexametaphosphate and 2.7% polyvinyl pyrrolidone was prepared. A second granulation was prepared of the same mixture but substituting 0.2% of a red colorant for the bicarbonate.

The single layer tablet was prepared by making a powder blend of 32.5% of the colored bicarbonate granulation, 8.5% of sodium carbonate, 0.05% of an anionic potassium perfluoroalkyl carboxylate (Fluorad FC-129), 0.4% spearmint oil, 11% potassium monopersulfate, 16% sodium monoperborate, 1.75% Alcalase 1.5P, 4% sodium lauryl sulfoacetate, 3.5% sodium metasilicate, 18.8% citric acid and 3.5% of polyethylene glycol. The resulting blend was then tableted.

The two layer tablet was prepared by forming two powder blends. In the first blend, 44% of the colored bicarbonate granulation was combined with 8.5% sodium carbonate, 0.1% of the Fluorad FC-129, 0.8% of the spearmint oil, 3.5% of Alcalase 1.5P, 8% sodium lauryl sulfoacetate, 7% sodium hexametaphosphate, 24.6% citric acid and 3.5% polyethylene glycol. The second blend was made by combining 21% of the uncolored bicarbonate blend with 8.5% sodium carbonate, 22% potassium monopersulfate, 32% sodium perborate monohydrate, 13% citric acid and 3.5% polyethylene glycol. The two granulations were fed separately into the respective hoppers of a two layer tableting press and tableted.

The sensory tests carried out unexpectedly show that changes in tablet aroma/odor with increasing storage time do not occur when the flavor oil or oils are isolated in one layer of a multilayer tablet and the bleaching agent or agents are located in another layer in accordance with the invention. The tests were carried out to evaluate the effects of aging on the organoleptic characteristics of denture cleansing tablets formulated as a single layer denture tablet composition and as a two layer composition in accordance with the invention. Tablet odor and solution odor were both tested.

For tablet odor evaluation, panelists were presented with three tablets of identical composition, a reference and two coded tablets. One coded sample was identical in age to the reference, both having been freshly prepared, and the other had been aged for seven months. The panelists were asked to identify the different samples on the basis of odor. For solution odor evaluation, a denture bath containing a tablet immersed in warm water was used and each panelist was presented with three denture baths. Each bath had just been prepared immersing one of the tablets (i.e. the reference or two coded tablets) in 140 ml of water at 40° C. The panelists were asked to identify the different samples on the basis of solution odor. The same test was carried out with 1) two layer tablets with the flavor oil isolated in one layer and the bleaching agent located in a second, separate layer; and 2) single layer tablets containing both flavor oil and bleaching agent.

Fifteen out of twenty panelists (p=0.12) were able to identify the different samples of single layer tablets and solutions having single layer tablets dissolved therein by virtue of their distinctive odor. This is greater than could be expected based upon random chance. The panelists readily distinguished between fresh single layer tablets and seven month old single layer tablets on the basis of tablet odor and odor of the solution resulting from dissolving the tablets in water. In contrast, the panelists could not distinguish fresh two layer tablets in accordance with the invention from seven month old two layer tablets in accordance with the invention on the basis of either tablet odor or solution odor.

The following tables summarize the results:

TABLE I

Odor Sensory Panel Results For Single Layer Formula Tablets

Tablet Odor: 15/20 panelists correctly identified the different sample-significant at the 95% confidence level (binomial evaluation).
Solution Odor: 15/20 panelists correctly identified the different sample-significant at the 95% confidence level.

DIFFERENCE FROM REFERENCE (Correct Answers):

| FRESH | | AGED (7 mos. old) | |
|---|---|---|---|
| Tablet Odor: | | | |
| Stronger | (6) | Not as Strong/Flat | (2) |
| More Minty | (1) | Less Minty | (3) |
| Peppermint Odor | (2) | Medicinal Odor | (1) |
| | | Not As Pleasant | (2) |
| Solution Odor: | | | |
| Stronger | (4) | Weaker | (3) |
| More Minty | (2) | Not as Minty | (4) |
| | | Not As Refreshing | (1) |

TABLE II

Odor Sensory Panel Results for Two Layer Formula Tablets

Tablet Odor: 12/20 panelists correctly identified the different sample-not significant (binomial evaluation). P = 0.120
Solution Odor: 13/20 panelists correctly identified the different sample-not significant. P = 0.074

DIFFERENCE FROM REFERENCE (Correct Answers):

| FRESH | | AGED (7 mos. old) | |
|---|---|---|---|
| Tablet Odor: | | | |
| Stronger | (3) | Not as Strong | (2) |
| More Minty | (2) | Less Minty | (1) |
| Peppermint Odor | (2) | Spearmint Odor | (1) |
| Milder | (1) | No Odor | (1) |
| Different Strength | (1) | Not Minty | (1) |
| Solution Odor: | | | |
| Stronger | (1) | Weaker/No Odor | (2) |
| More Minty | (1) | Not as Minty | (1) |
| | | Not As Refreshing | (1) |

EXAMPLE 2

A blue colored granulation is prepared by charging the bowl of a fluid bed granulator with 82.6 parts of sodium bicarbonate and 14.6 parts of sodium hexaphosphate. After the charge has been fluidized for several minutes, the mixture is sprayed at an inlet temperature between 55° and 65° C. with a 15% aqueous solution containing 30 parts of polyvinylpyrrolidone and 0.3 part of FD&C Blue No. 2 at a rate of 800–1400 g/min, increasing air flow as necessary while spraying to maintain fluidization. When spraying is complete, the product is dried at an inlet air temperature of 70°–80° C. until the difference between the product temperature and inlet air temperature is constant. The granulation is then passed through a lump breaker equipped with a coarse screen. A white granulation is prepared in the same manner except that the blue dye is omitted.

The blue granulation in an amount of 44 parts and 8.5 parts of sodium carbonate is charged to a ribbon blender and mixed to produce a uniform blend. Then 0.1 part of Fluorad FC-129 is charged to the blender followed by 0.8 part of spearmint oil. When these materials have been uniformly mixed, 24.6 parts of citric acid, 3.5 parts of protolytic enzyme (Alcalase 1.5P), 8 parts of lathanol, 7 parts of sodium metasilicate, 3.5 parts of Carbowax 8000 and 0.02 part of FD&C Blue No. 2 are added and mixed to form a uniform blend. Separately 21 parts of the white granulation and 8.5 parts of sodium carbonate are mixed, followed by charging 22 parts of oxone, 32 parts of sodium perborate monohydrate, 13 parts citric acid and 3.5 parts of Carbowax 8000 and mixing until a uniform product was obtained. The two granulations are then fed separately into the respective hoppers of a two layer tabletting press and tabletted.

EXAMPLE 3

A green tabletting granulation was prepared by first charging 82.5 parts sodium bicarbonate and 14.6 parts sodium carbonate into a mixing bowl. After three minutes of dry blending, a 32.3% aqueous solution containing 30 parts of polyvinylpyrrolidone, 1 part of FD&C Blue No. 2 and 1.3 parts of FD&C Yellow No. 5 were added to the mixing bowl during the first 45 seconds of a five minute mixing period. The mixing blades and sides of the bowl were scraped several time with a spatula to ensure no material was allowed to hang onto the bowl or the blades. The formulation was then mixed for an additional 5 minutes giving a total mixing time of 10 minutes. The resulting mixture was transferred to a tray dryer on which it was dried at 70° C. until the loss on drying was 0.5% or less. After this drying, the granulation as then screened to remove any oversized particles and the green granulation was stored.

A white granulation was prepared in the similar manner such that it contained 82.7 parts sodium bicarbonate, 14.6 parts sodium carbonate and 2.8 parts of polyvinylpyrrolidone.

Charged to a ribbon blender was 44 parts of the green granulation and 8.5 parts of sodium carbonate. This mixed until a uniform blend was obtained and then 0.1 part Fluorad FC-129 and 0.8 part of spearmint oil were added. When these materials has been uniformly mixed, 3.5 parts Alcalase 1.5P, 8 parts Lathanol, 7 parts sodium metasilicate, 24.6 parts citric acid, 3.5 parts Carbowax 8000, 0.01 part FD&C Blue No. 2 and 0.02 part FD&C Yellow No. 5 were added and mixing continued until a uniform blend was prepared. In like manner, a white blend was prepared using 21 parts of the white granulation, 8.5 parts sodium carbonate, 22 parts Oxone, 32 parts sodium perborate monohydrate, 13 parts citric acid and 3.5 parts Carbowax 8000.

The green and white layer blends were fed separately into the respective hoppers of a two layer tabletting press and tabletted.

Although the present invention has been described in relation to a particular embodiment thereof, many other variations and modifications and other uses will become apparent to those skilled in the art. All parts and percentages expressed herein are by weight percent and all temperatures are in degrees centigrade unless otherwise stated.

What is claimed is:

1. A multilayer denture cleanser tablet composition having at least two layers, containing a flavoring effective amount of a flavoring agent and a bleaching effective amount of a bleaching agent, the flavoring agent and bleaching agent being kept apart such that the flavoring agent is located in a first layer and the bleaching agent is located in a second, separate layer, whereby deterioration of the flavoring agent by the bleaching agent is reduced.

2. The composition of claim 1, wherein the flavoring agent is selected from the group consisting of mint oil, menthol, oil of wintergreen and a citrus flavor.

3. The composition of claim 2, wherein the mint oil is selected from the group consisting of peppermint and spearmint.

4. The composition of claim 2, wherein the citrus flavor is selected from the group consisting of lemon, lime and orange.

5. The composition of claim 1, wherein the flavoring effective amount of the flavoring agent is between about 0.05% to about 4%.

6. The composition of claim 5, wherein the flavoring effective amount of the flavoring agent is between about 0.1% to 2%.

7. The composition of claim 1, wherein the bleaching agent is selected from the group consisting of a peroxygen bleach and a chlorine or hypochlorite generating compound.

8. The composition of claim 1, wherein the effective amount of the bleaching agent is between about 1% to about 80%.

9. The composition of claim 8, wherein the effective amount of the bleaching agent is between about 5% to about 55%.

10. The composition of claim 1 wherein an enzymatic effective amount of an enzyme is located in a third layer.

11. A multilayer, enzymatic denture cleanser tablet composition, comprising a first layer containing a flavoring effective amount of a flavoring agent, and a second, separate layer containing a bleaching effective amount of a bleaching agent and an enzymatic effective amount of an enzyme, wherein all the enzyme is located in the second layer and all of the flavoring agent is located in the first layer.

12. The composition of claim 11, wherein the flavoring agent is selected from the group consisting of a mint oil, menthol, oil of wintergreen and a citrus flavor.

13. The composition of claim 12, wherein the mint oil is selected from the group consisting of peppermint and spearmint.

14. The composition of claim 12, wherein the citrus flavor is selected from the group consisting of lemon, lime and orange.

15. The composition of claim 11, wherein the effective amount of the flavoring agent in between about 0.05% to about 4%.

16. The composition of claim 15, wherein the effective amount of the flavoring agent in between about 0.4% to 1%.

17. The composition of claim 11, wherein the bleaching agent is selected from the group consisting of a peroxygen bleach and a chlorine or hypochlorite generating compound.

18. The composition of claim 11, wherein the effective amount of the bleaching agent is between about 1% to about 80%.

19. The composition of claim 18, wherein the effective amount of the bleaching agent is between about 5% to about 55%.

* * * * *